United States Patent [19]

Middleton

[11] 4,122,115

[45] Oct. 24, 1978

[54] PREPARATION OF CHLORO- AND BROMO-FLUOROACETYL CHLORIDE

[75] Inventor: William Joseph Middleton, Chadds Ford, Pa.

[73] Assignee: E. I. Du Pont de Nemours and Company, Wilmington, Del.

[21] Appl. No.: 849,023

[22] Filed: Nov. 7, 1977

[51] Int. Cl.$^2$ .............................................. C07C 51/58
[52] U.S. Cl. ................................................ 260/544 Y
[58] Field of Search ..................................... 260/544 Y

[56] References Cited

U.S. PATENT DOCUMENTS 3,742,047  6/1973  Prill ................................. 260/544 Y

FOREIGN PATENT DOCUMENTS 679,185  9/1952  United Kingdom ..................... 260/544

OTHER PUBLICATIONS

Schmidt et al., Ber. 98, pp. 1003–1004, (1965).

Primary Examiner—Gerald A. Schwartz
Attorney, Agent, or Firm—Anthony P. Mentis

[57] ABSTRACT

An alkyl ester of a chloro- or bromo-fluoroacetic acid is reacted with chlorosulfonic acid to produce the corresponding acid chloride. Exemplary is the reaction of ethylchlorofluoroacetate with chlorosulfonic acid at 120°–200° C to produce chlorofluoroacetyl chloride.

7 Claims, No Drawings

PREPARATION OF CHLORO- AND BROMO-FLUOROACETYL CHLORIDE

BACKGROUND OF THE INVENTION

1. Field of the Invention

This invention is the process of reacting chlorosulfonic acid with a selected ester of a halofluoroacetic acid to produce the corresponding acid chloride.

2. Prior Art

Acid chlorides are generally prepared by reacting an acid with a compound such as $PCl_5$. Young et al., J.A.C.S. 71, 2432 (2433) (1949), described the preparation of chlorofluoroacetyl chloride in two steps. The corresponding ester is first hydrolyzed to the acid and the acid is then treated with $PCl_5$ to give the acid chloride.

U.S. Pat. No. 3,742,047 to E. J. Prill discloses, as in Example 8, reacting chlorosulfonic acid with an acid to yield an acid chloride.

M. Schmidt et al., Ber. 98, 1003 (1965) shows the preparation of acyl chlorides by the reaction of an acyl anhydride with chlorosulfonic acid.

British Pat. No. 679,185 (1952) issued to Henkel and Cie shows the reaction of an alkyl benzene sulfonic acid with chlorosulfonic acid to produce an alkyl benzene sulfonic acid chloride.

R. B. Wagner et al., Synthetic Organic Chemistry (1953) pages 547 and 548 show the preparation of ethoxalyl chloride by the reaction of phosphorus pentachloride on ethyl oxalate, or by the reaction of thionyl chloride on potassium ethyl oxalate.

Synthesis of chlorofluoroacetyl chloride from the corresponding acid is not practical on a kilogram scale because of the difficulties in isolating and purifying the highly water soluble and hygroscopic acid. A synthesis based on converting the anhydrous sodium salt of chlorofluoroacetic acid to the acid chloride has also shown difficulties on scale-up. The sodium salt is an extremely hygroscopic, hard, intractable solid that cannot be easily removed from the vessel in which it is deposited by evaporation. Also, it is thermally unstable and subject to decomposition during the drying process.

THE INVENTION

It has now been found that a convenient one-step process for converting an alkyl ester of chlorofluoroacetic acid or bromofluoroacetic acid to the corresponding acid chloride is to simply heat a mixture of the ester and chlorosulfonic acid and distill off the acid chloride as it it formed.

The invention may thus be stated to be the process of heating a compound of the formula $CHFXCO_2R$ where X is chlorine or bromine and R is alkyl of 1 to 4 carbons with chlorosulfonic acid at a temperature in the range 70° to 250° C. and distilling off CHFXCOCl as it is formed. A preferred temperature range is 70°–200° C.

The molar ratio of the two starting materials is not critical but at least one equivalent of chlorosulfonic acid should be used for best yields. The reaction proceeds well and no diluents or solvents are necessary. An inert liquid diluent such as a high boiling hydrocarbon as for example mineral oil, or an aromatic solvent such as o-dichlorobenzene or phthaloyl chloride, can be added to the reaction mixture if desired.

The reaction is most conveniently carried out at atmospheric pressure but higher or lower pressures can be used if desired.

A preferred embodiment of the invention is the addition to the reaction mixture of an aromatic carboxylic acid chloride such as phthaloyl chloride or benzoyl chloride to improve the yield of the halofluoroacetyl chloride formed. The aromatic carboxylic acid chloride can be present to the extend of 0.1 to 3 molar equivalents based on the starting ester.

SPECIFIC EMBODIMENTS OF THE INVENTION

In the following representative examples all parts and percentages are by weight and all temperatures are Centigrade unless otherwise stated.

EXAMPLE 1

Chlorofluoroacetyl Chloride

A mixture of 141 g (1 mole) of ethyl chlorofluoroacetate and 143 ml (2.2 mole) of chlorosulfonic acid was heated in a simple still and the distillate was collected in an ice-cooled trap backed up by a dry ice-cooled trap. Distillation was continued until the pot temperature reached 180° and head temperature reached 87°. The distillate in the two traps were combined and redistilled through a spinning-band column to give 65 g (50%) of chlorofluoroacetyl chloride as a colorless liquid, bp 68°–69°.

EXAMPLE 2

Chlorofluoroacetyl Chloride

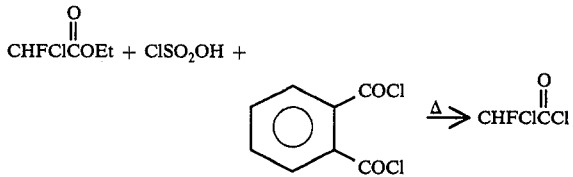

A mixture of 281 g (2 mole) of ethyl chlorofluoroacetate, 406 g (280 ml, 2 mole) of phthaloyl chloride, and 144 ml (256 g, 2.2 mole) of chlorosulfonic acid was heated at total reflux for 2 hours in a still connected to an ice-cooled receiver backed up by two dry ice-cooled traps.

During the 2 hour period HCl, $SO_2$, ethyl chloride and ethylene were evolved when the pot temperature reached 90°. These gases were collected in a cooled trap. At 100° distillation began and volatile material was distilled out as the temperature slowly rose to 200°. The condensate trapped in the dry ice-cooled traps was slowly warmed to room temperature to boil off the gaseous materials and then combined with the distillate in the ice-cooled receiver. Distillation of this combined material through a spinning-band column gave 188.6 g (72% yield) of chlorofluoroacetyl chloride as a colorless liquid, bp 69°.

EXAMPLE 3

Bromofluoroacetyl Chloride

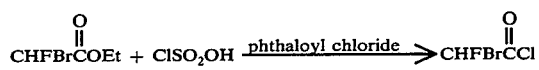

A mixture of 51 g (0.33 mole) of ethyl bromofluoroacetate, 47 ml (67 g, 0.33 mole) of phthaloyl chloride, and 25 ml (0.37 mole) of chlorosulfonic acid was heated in a simple still from ambient temperature to a pot temperature of 200° and the material that distilled from the reaction mixture was collected in an ice-cooled receiver. The distillate was redistilled through an 18 inch spinning band column to give 35.83 g (62% yield) of bromofluoroacetyl chloride as a colorless liquid, bp 90°–93° (mostly 92°); $^1$H nmr (CFCl$_3$) $\delta$ 6.65 ppm (d, J = 51 Hz); $^{19}$F nmr (CFCl$_3$) $\delta$ −141.7 ppm (d, J = 51 Hz).

Anal. Calcd for C$_2$HBrClFO: C, 13.70; H, 0.58; F, 10.83. Found: C, 13.85; H, 0.71; F, 10.71.

The following table illustrates additional examples of the preparation of halofluoroacetyl chlorides, using the procedures set forth above.

| Ester | No. of Equivalents of ClSO$_2$OH | Added Material | Products |
|---|---|---|---|
| CHFClCOCH$_3$ | 2 | o-dichlorobenzene | CHFClCCl |
| CHFBrCOCH$_3$ | 1.1 | phthaloyl chloride | CHFBrCCl |
| CHFClCOCH$_2$CH$_2$CH$_2$CH$_3$ | 2 | none | CHFClCCl |
| CHFBrCOCH(CH$_3$)$_2$ | 3 | mineral oil | CHFBrCCl |
| CHFClCOC$_2$H$_5$ | 1.5 | benzoyl chloride | CHFClCCl |

Chlorofluoroacetyl chloride and bromofluoroacetyl chloride are known acyl chloride compounds and can be used as acylating agents in common with all acyl chlorides. They are also valuable in preparing intermediates for use in the production of valuable tranquilizers as shown in commonly assigned applications Ser. No. 807,075 filed June 16, 1977 and Ser. No. 807,077 filed June 16, 1977.

I claim:

1. The process of heating a compound of the formula

CHFXCOOR wherein
X = Cl or Br and
R = alkyl of 1–4 carbons
with chlorosulfonic acid at a temperature of 70°–250° C. and recovering a compound of the formula CHFXCOCl.

2. The process of claim 1 wherein the temperature is 70°–200° C.

3. The process of claim 1 wherein an aromatic carboxylic acid chloride is present during the heating.

4. The process of claim 3 wherein phthaloyl chloride is present.

5. The process of claim 3 wherein benzoyl chloride is present.

6. The process of claim 1 wherein the starting ester is ethyl chlorofluoroacetate.

7. The process of claim 1 wherein the starting ester is ethyl bromofluoroacetate.

* * * * *